(12) United States Patent  (10) Patent No.: US 6,186,147 B1
Cobb  (45) Date of Patent: Feb. 13, 2001

(54) METHOD FOR ELECTROSURGICAL TISSUE CUTTING AND COAGULATION

(75) Inventor: Garry V Cobb, Chilwell (GB)

(73) Assignee: Nuvotek Limited, Leeds (GB)

( * ) Notice: Under 35 U.S.C. 154(b), the term of this patent shall be extended for 0 days.

(21) Appl. No.: 09/361,062

(22) Filed: Jul. 26, 1999

Related U.S. Application Data

(62) Division of application No. 08/973,153, filed as application No. PCT/GB96/01302 on May 3, 1996, now Pat. No. 6,010,499.

(51) Int. Cl.[7] .................................................. A61B 19/00
(52) U.S. Cl. ............................................................ 128/898
(58) Field of Search ................................. 606/39, 40, 41, 606/42, 45, 48–52; 607/101, 122; 128/898

(56) References Cited

U.S. PATENT DOCUMENTS 5,374,596  12/1994  Klicek et al. ........................... 606/35
5,514,129  5/1996  Smith ..................................... 606/40

FOREIGN PATENT DOCUMENTS

3904558 A1  8/1990  (DE) .
0 237 795  2/1987  (EP) .
WO 94/10922  5/1994  (WO) .
WO 95/25472  9/1995  (WO) .

*Primary Examiner*—Linda C. M. Dvorak
*Assistant Examiner*—R. Kearney
(74) *Attorney, Agent, or Firm*—Woodard, Emhardt, Naughton Moriarty & McNett

(57) ABSTRACT

The apparatus and method of the current invention relate to electrosurgical work involving the forming of cuts in and coagulation of body tissue of a patient. The apparatus and method of the invention overcome disadvantages common with conventional dipolar and monopolar apparatus. In one aspect the invention provides a cutting tool or instrument with at least one cutting or coagulation tip and the tool is adapted to operate as both a power supply electrode to supply power to the tip and as a return electrode to allow impedance feedback signals to be received by a control means thereby eliminating the need for a separate second electrode and taking the patient out of the circuit received by a control means According to a second aspect the feedback information is stored, processed and analyzed in relation to pregrogrammed and previous actual feedback to allow alteration to the power supply to the tip to create optimum cutting and/or coagulating conditions.

4 Claims, 7 Drawing Sheets

The Median Filter uses the median value from an array of sample values

The Median Value is the middle value of a group of sample blocks when the group is sorted in ascending order (assuming the number of samples is ODD)

Example: Input Sequence = (6, 7, 14, 5, 8, 5, 12)
         Sort Sequence = (5, 5, 6, 7, 8, 14, 15)

Median value = 7 (Average value = 8.6)

Post Recursive Filtering

The following example illustrates how a difference in weighting of new values changes the speed of response to value changes (numbers are arbitrary)

The following is a set of arbitrary values, representing a large sudden change at a certain point. (A) represents a 0.10 weight and (B) represents a 0.25 weight Recursive Filter. Values were received in the following order;

1  1  1  1  1  10  10  10  10  10

(A) calculation = (n−1)*0.9+(n)*0.1  (new value (n) weighted at 0.1, or 10% of total.)

Output values of the above calculation are as follows;

−  1  1  1  1  1.9  2.71  3.44  4.10  4.68

(B) calculation = (n−1)*0.75+(n)*0.25 (new value(n) weighted at 0.25, or 25% of total.)

Output values of the above calculation are as follows;

−  1  1  1  1  3.25  4.90  6.28  7.14  7.86

(n−1) = previous calculated value(n) = new incoming value

*Fig. 3*

Definition of the parameter du

METHOD FOR ELECTROSURGICAL TISSUE CUTTING AND COAGULATION

The present application is a divisional of U.S. patent application Ser. No. 08/973,153 filed Dec. 1, 1997, now U.S. Pat. No. 6,010,499 which is a 371 of PCT/GB96/01302 filed May 3, 1996.

The current invention relates to apparatus for use in the electrosurgical field and in particular in relation to the provision of apparatus for cutting body tissue and/or coagulation such as is required in, for example, endoscopic surgery which is increasingly common.

When using apparatus of this type to, for example, cut parenchymal organs the surgeon wishes to obtain efficient heamostasis either as a result of coagulation to a greater or lesser depth as the cut is being made or as a result of partial coagulation of the bleeding vessels once the cut is completed. The efficiency with which the bleeding can be stopped depends upon the intensity of thermal coagulation; and the greater the depth of coagulation inside the tissue, the greater the heamostatic effect. At the same time however it must be ensured that no more tissue suffers thermal damage during cutting and coagulation than is absolutely necessary in order to obtain the desired effect as the damage caused is irreparable. This is an important consideration as increasingly, higher output currents are used to cut. As the higher currents and hence power is provided so the risk of electric current channelling along unseen or obscured body organs adjacent the cutting area is increased and can cause damage to vital anatomical structures and increase the risk of peripheral burns to the patient.

For many years work has been undertaken in an attempt to provide apparatus which allows accurate high powered cutting and coagulation of the body tissue and fluids and which has a minimum risk to the patient upon whom the surgery is performed and also to the surgeon and/or apparatus operator.

In general, when an electrode, which acts as a cutting tool, contacts body tissue an electric arc or spark is created which causes a zone of thermal necrosis to be created beneath and around the area of contact. As the current is applied it passes through individual cell membranes in the patient causing the same to be vapourised and the cut to be created.

One known group of apparatus type is known as monopolar apparatus which utilises an electrode which forms the cutting and coagulation tool and through which an alternating current of, for example, between 300 kHz and 1 mHz flows. When the electrode is held at a distance from the body no current flows and no cutting action occurs but as the electrode is brought closer to the body tissue a spark will jump across the gap to the tissue if, for example, the voltage is between 1000 to 10000 volts peak to peak.

This apparatus is provided with a separate return electrode which must have a sufficiently large area to minimise the heating effect caused by the current passing through the patient and prevent tissue surface burns. Typically therefore the return electrode is required to be in the form of a plate upon which the patient lies. These plates can be disposable but in any case are relatively expensive. Thus, in this type of apparatus, relatively high powered cutting currents can be obtained but there are inherent risks to the patient who does, in effect, form part of the electrical circuit and is therefore exposed, sometimes dangerously, to burns and tissue damage caused by contact with the plate. In an attempt to minimise the problem the resistance of the return electrode plate is monitored but this tends to be a reactive rather than a proactive monitoring technique which does not monitor the condition of the patient body tissue and therefore does not eliminate the risk to the patient. Thus the monopolar cutting system, although widely used, has many deficiencies which, if they are not to cause damage to the patient, are required to be carefully monitored with additional expensive apparatus.

An alternative group of apparatus is the bipolar cutting apparatus which utilises two electrodes which contact the tissue to be cut and coagulated in close proximity to each other. One electrode operates to supply power to cut and coagulate the tissue and the other acts as a return electrode with the current density on both electrodes being kept the same. In this apparatus it is not necessary to have a return or dispersive electrode in the form of a plate and therefore the patient is safer but known bipolar apparatus cannot generate sufficient power to allow fast, efficient high powered cutting such as that required for procedures such as Trans Urethral Resection of the Prostate in Urology and Transcervical Resection of the Endometrium in Gynaecological Surgery.

A further type of apparatus is disclosed in patent document U.S. Pat. No. 5,334,193 which addresses the problem of applied cutting power in electrosurgical use and also discloses in discussing prior art documents how apparatus can be provided to have cut off or alarm thresholds to prevent continued power supply when potentially damaging operating conditions are sensed. However the prior art does not provide for the continued monitoring and analysis and alteration of the power supple during the operation of the apparatus. The document U.S. Pat. No. 5,334,193 discloses the ability to monitor the impedance of the body tissue but only as a means of determining whether the calculations undertaken in respect of the other data received in the form of the active and return current signals are valid and should be applied to the overall control parameters of the apparatus and/or whether the measurements should be taken more or less frequently. The impedance values are not used in the setting of the control parameters in this patent but as a further check of the operation of the apparatus.

Thus the known apparatus systems have many disadvantages and further general disadvantages are that the systems can cause interference to other equipment in the theatre namely anaesthetic apparatus, video monitoring equipment, pacemakers fitted to patients and, due to the system operation, and the presence of currents through the body tissue non conductive cutting fluids are required to be used such as glycine which is toxic and, if absorbed in too great a quantity by the patient, can render them seriously ill or even kill them.

The aim of the current invention is to provide apparatus for the cutting and/or coagulation of body tissue and organs which can provide a controlled output power supply and with sufficient power to allow all required operations to be performed yet minimise the equipment required to be used.

The current invention, in a first aspect, provides apparatus for electrosurgical use to cut and/or coagulate body tissue, said apparatus comprising an electrical generator and control means connected to a tool, said tool selectively operable to provide cutting and/or coagulation via a tip formed at an end thereof, and including first and second electrodes in connection with said tip and in turn said body tissue and characterised in that the control means includes means for measuring the phase angle and the modulus of the impedance indicative of the body tissue and regulates the power supply to the tool dependent on said measurements to ensure that the optimum cutting power is supplied at each instant.

Typically upon the starting of the operation of the apparatus the same current waveform is provided along the power supply and feedback electrodes until the measured impedance alters and this arrangement ensures that the tissue under the influence of the tip is prevented from leaking to areas other than adjacent to the tip.

The electrodes are preferably provided as part of the tool and the control means is operated to allow power to be carried to the tool tip and the measurement of the phase angle and the modulus of the impedance feedback to be received and measured by the control means.

Typically the current supplied is only exposed at the tip of the tool and therefore there is no risk of damage to tissue or organs with which any other part of the tool comes into contact.

Thus the impedance of the body tissue adjacent the tip of the tool can be monitored by the control means.

Typically the control means includes a means for receiving the phase angle and the modulus of the impedance of the body tissue, comparing and interpreting the same and adjusting the strength of current and/or voltage transmitted along the tool to the tip according to the values to alter the cutting power to ensure that the optimum cutting power is supplied at each instant. This ensures that the optimum cut and/or coagulation operations can be provided.

Thus there is provided apparatus for use in electrosurgery, said apparatus including a tool having a tip at one end thereof, said tool acting as an electrode connected to an electrical supply generator; and control means and wherein the control means receives a constantly updated indication of the phase angle of the impedance at the point of the cutting tip of the tool and the modulus of the impedance of the body tissue adjacent the point of cut.

The measuring and comparison of the phase angle and modulus of the impedance as opposed to the phase angle impedance alone as in conventional apparatus allows the condition of the body tissue to be taken into account and a more accurate and representative signal to be provided to the control means.

Preferably the impedance feedback is returned to the control means via an electrode which can, in one embodiment, be separate from the tool or, in another embodiment, is returned using the tool. Where the tool has a supply and return electrode this embodiment has the advantage of only requiring one tool to be held at the cutting point as opposed to the monopolar system where the cutting tool and a return plate under the patient is required and the bipolar system where two physically separate electrodes are required to be provided adjacent the point of cut.

Typically the apparatus control means includes means for receiving the impedance measurements, assessing the same relative to preceding impedance measurements received, comparing the information with preprogrammed information and, if required, altering the current and/or voltage supply values to alter the power supply to the tool tip.

Such alterations in impedance values can be caused by the tip passing into or through the initial body surface, body tissue of different form and/or organs and the ability to sense this and alter the power output allows the cut to be achieved with a minimum of damage to the body tissue surrounding the cut area.

In a further aspect of the invention there is provided a method for the control of the power supply to the cutting tip of electrosurgical apparatus characterised in that the method includes applying a tool with cutting tip in position relative to the body tissue to commence work, measuring the phase angle and the modulus of the impedance indicative of the body tissue in a control means connected to said tool, assessing the measurement in the control means in conjunction with preceding impedance measurements and, if required, altering the power supply to the tool tip, and repeating the process at stages during use or the apparatus to ensure that the optimum cutting power is supplied at each instant.

In a preferred embodiment the values equivalent to the phase angle and the modulus of the impedance received are split into a series of sample blocks which are held in a memory of the control means and constantly updated as further measurements are received. Each of the sample blocks is preferably representative of a small time interval and a set number of blocks analysed in combination at any one time to ensure that short events such as, for example, short circuits, do not have a dramatic or damaging effect on the power supply parameters. Furthermore the alteration in impedance values required to cause an adjustment in the power supplied is set such that relatively minor variations are "levelled out" and filtered from the results used and do not cause the power supply means to be continuously altered.

By utilising the sample blocks the trend of the measurement readings for the blocks which make up each sample can be averaged and, if the average value shows a trend which is significant in comparison with the preprogrammed information the output value control algorithm is adjusted accordingly and, as a result, the power output to the tip is adjusted. Typically the control analysis is performed using an adaptive intelligent algorithm which is provided in the software of the control means and this algorithm is developed with preprogrammed parameters from a tissue reactance database which indicates the expected Electrosurgical power, current voltage and tissue impedance values for specific types of tissue and electrosurgical operations and depending upon the settings selected by the apparatus user.

Preferably, and in order to prevent damaging alteration to the supply of power to the tip, limiting values can be set by the operator of the apparatus. Typically an upper limit is set above which the output power supply will not go even if instructed by the control means analysis.

A further feature of the control means of this type is that conventional monopolar and/or bipolar cutting tools can be used in conjunction with the control means and a specially designed, electrical cable and still achieve the advantageous control of the current and voltage parameters as described above.

A specific embodiment of the invention is now described with reference to the accompanying drawings wherein;

FIG. 3 illustrates an example of the post recursive filtering of feedback results;

Figure 5:
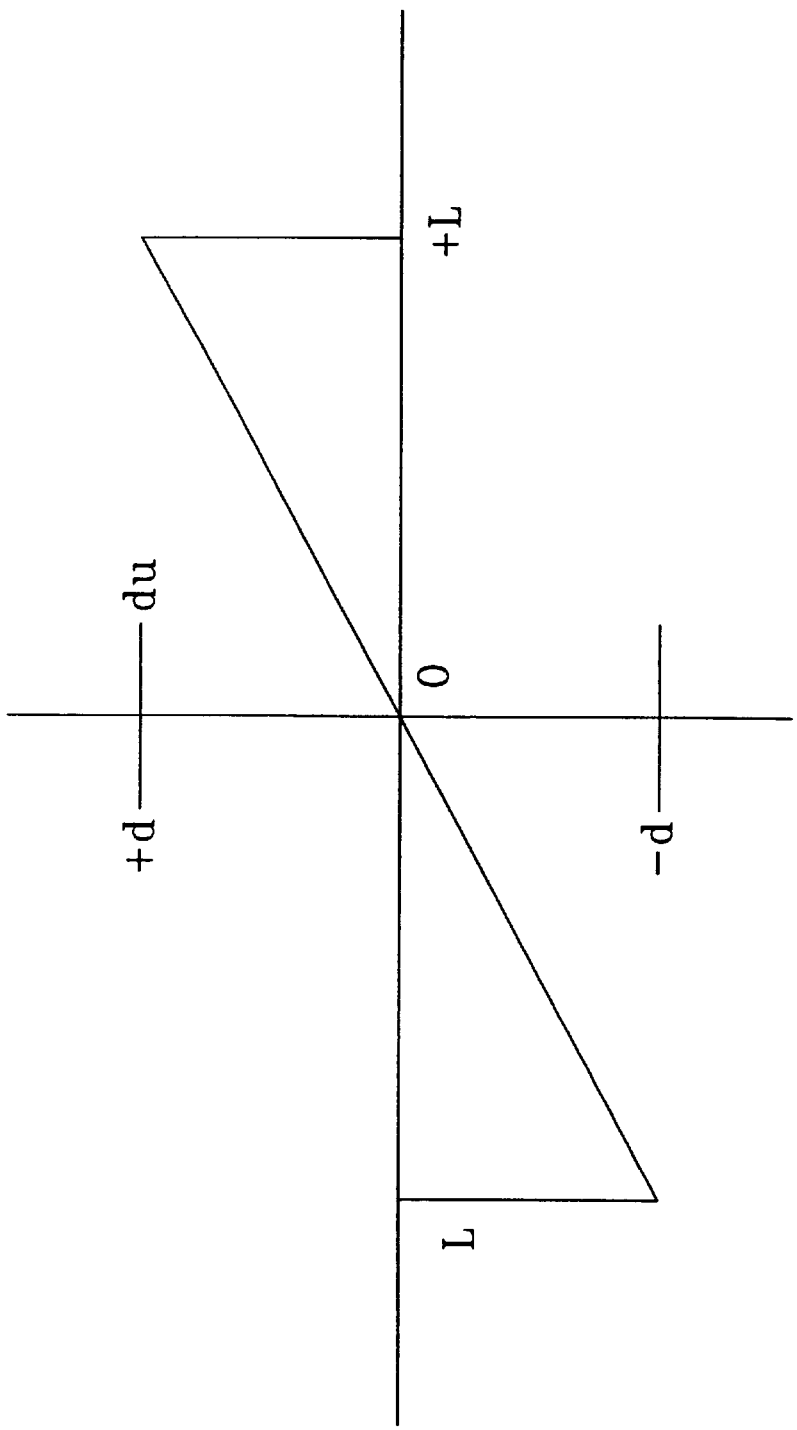
Figure 6:
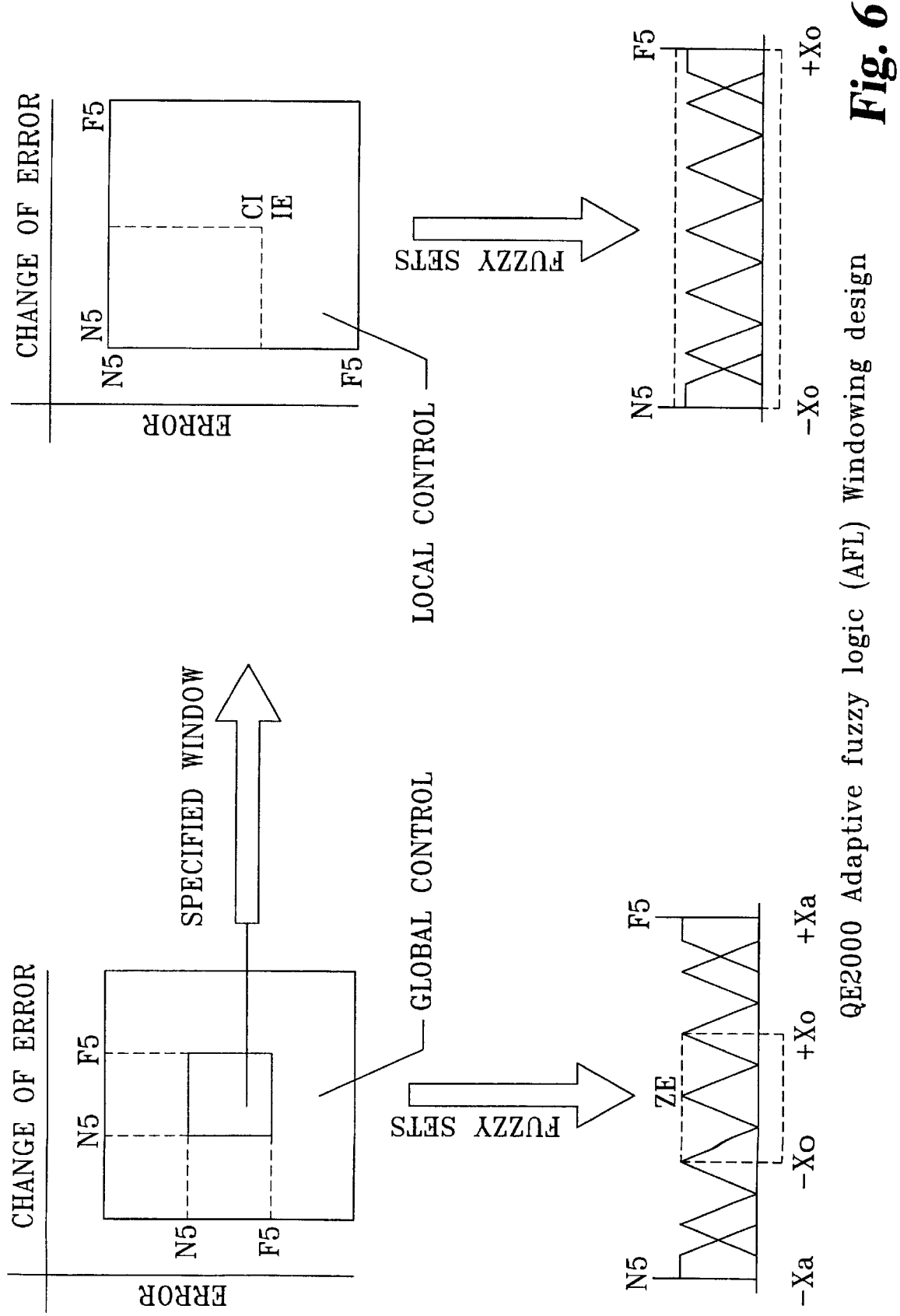
Figure 7:
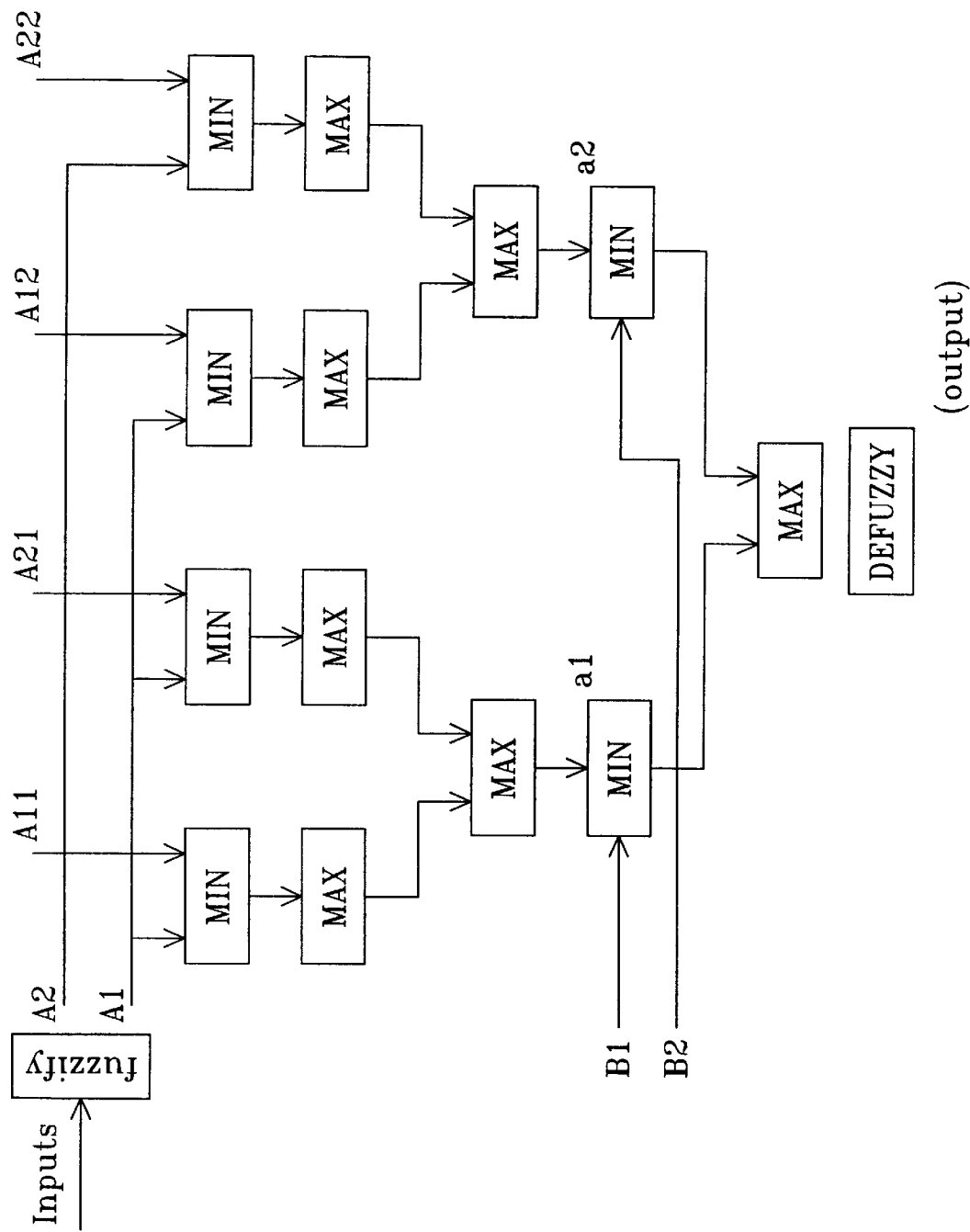

FIGS. 5 and 6 relate to the provision of fuzzy logic controllers (FLC) in the control means; and FIG. 7 relates to the provision of a fuzzy logic process or (FLP) in the control means.

Figure 1:
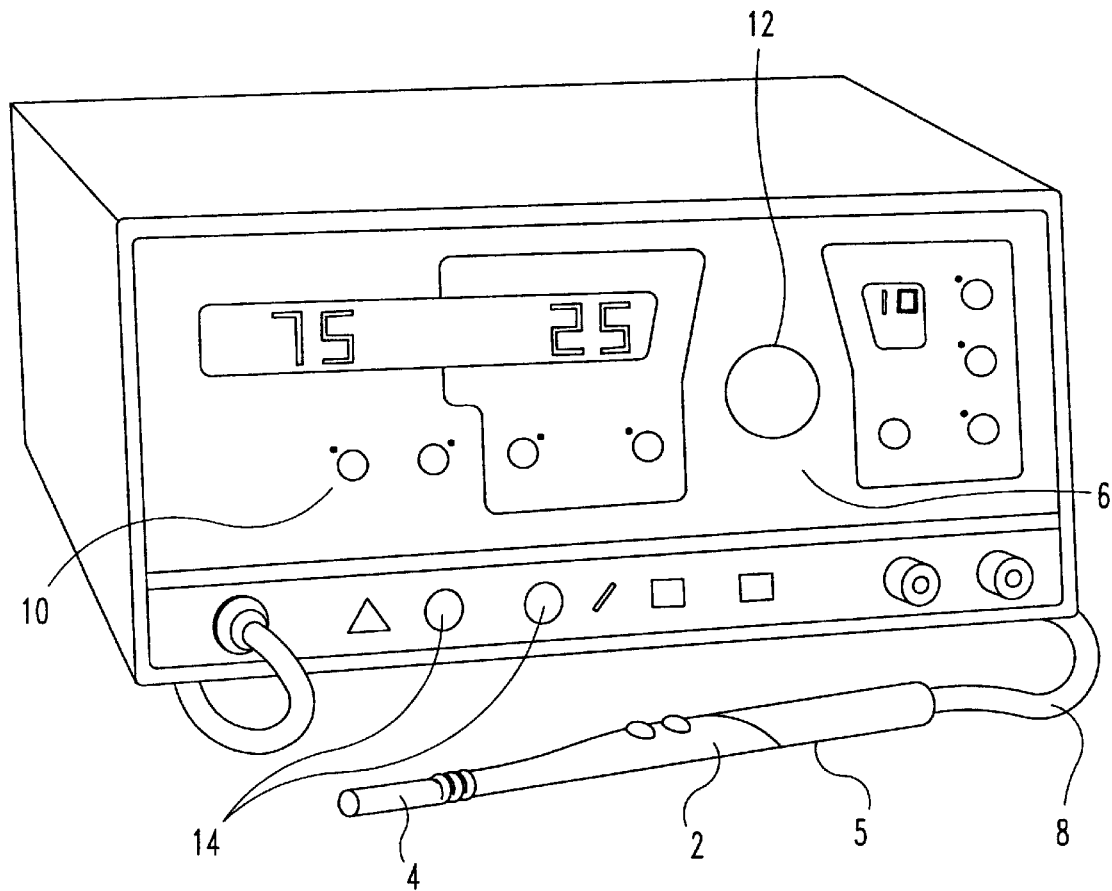
FIG. 1 illustrates a perspective view of the apparatus in one embodiment.

Referring firstly to FIG. 1 there is shown apparatus according to the invention, said apparatus comprising a tool 2 which is provided with a cutting tip 4 and selector buttons 5 for the selection of cutting or coagulating operations or both. The tool is supplied with power and the current is exposed only at the tip 4 and can be used to cut into and/or coagulate body tissue depending on the settings selected on the control means and electrical power generator 6. The tool 2 is connected to the control means 6 by an electrical cable 8 which allows power to be supplied to the tool 2 and measurements of the phase angle and the modulus of the impedance of the body tissue to be received back from the area adjacent the tool cutting tip 4 when in use. The tool is typically formed of any conducting material but preferably stainless steel or titanium. Typically, with the exception of the tip 4 the tool has an outer casing of insulating material.

The control means 6 includes a microprocessor which allows analysis of the measurements of the impedance of the body tissue at the tip of the tool 2 and this analysis allows the power supply to the tool 2 to be adjusted if required. The control means includes a series of selector buttons 10 on the facia which include the functions of the switching on/off of the device, the selection of preprogrammed parameter selections from the memory, the selection of cut only, coagulate only or blended cut and coagulation operations and the auto or manual control of the same. In whichever mode, the power value to be supplied to the tool can be set by the person using the apparatus via a rotary control knob 12 which allows rapid selection of the power value, and, when selected, the value is set so that further unauthorised or accidental turning of the knob cannot alter the setting.

A further feature is that the apparatus can be simultaneously used by more than one person using the independent outputs 14 provided.

Thus the cutting tool 2 according to the invention is provided to allow power to be supplied to the tip 4 to allow cutting and/or coagulation to take place and is provided to allow the measurement of the phase angle and the modulus of the impedance of the body tissue at the tool tip to be received by the control means and therefore allow only one tool to be used. The measurements received thus allows the operation of the control means as herein described.

The provision of the microprocessor controlled control means ensues optimum supply of power to the tool 2 to allow the required operation to be performed with minimum damage to the surrounding body tissue.

The microprocessor software includes an adaptive algorithm therein which allows the correct and optimum power output characteristics to be provided to the tool 2 using a combination of a default coefficient and an adaptive coefficient developed from a body tissue reactance database which provides preprogrammed parameters for the power output from known results.

In use, the tissue impedance is calculated continuously using the default coefficient until 13 samples blocks, each containing a value derived from impedance measurements from the tool tip of the modulus and the phase angle impedance and other parameters over a set time interval, are recorded in the memory. The preprogrammed algorithm power output values from the database are then compared to the results obtained using the sample block values and if the sample block values results are significantly different the initial power output values are compared again and if required the output power value to the tool tip is altered by altering the current and/or voltage. The algorithm is also adjusted to take into account these changes in parameters but it should be noted that the changes to the power output are limited by any limit settings which are input by the person using the apparatus.

A final step of the control means is to compare the output power values obtained from the adjusted algorithm to the values which would have been obtained from using the original or default algorithm. If the default equation would have provided better output values then this is again used for the next comparison with the next sample blocks.

Figure 2:
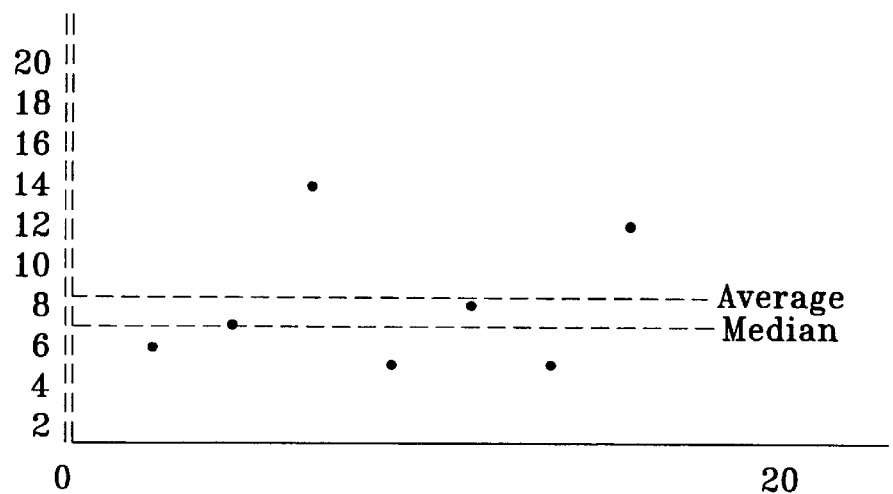
FIG. 2 illustrates an example of the median filtering of feedback results.

To further improve the control means a median filtering system is used to prevent individual or freak feedback values from the return electrode from altering the power output value. This ensures that a median value is provided for each set of sample blocks at any one instant and included in the algorithm. This process continues with the oldest sample block value being replaced by the newest sample block value, the median value recalculated, and so on. An illustration of this process is shown in FIG. 2.

FIG. 3 illustrates a further feature of the analysis process wherein post recursive filtering is used after the median filtering as this takes the median value of each parameter and inputs the same into the power output algorithm. The filter process acts to give a weighting to each median before entering it into the algorithm and this weighting is reduced as the time from occurrence increases and therefore the most recent median value is given the heaviest weighting and thereafter decreases as the new median values are entered.

The filtering processes described above and illustrated in FIGS. 2 and 3 ensure that while the output setting is changed to suit the impedance values received from the tool and body tissue during the use of the tool 2, the changes are not dramatic changes and the power output does not alter to an extent and with a frequency that could cause damage to the patient and/or render the apparatus unusable.

Figure 4:
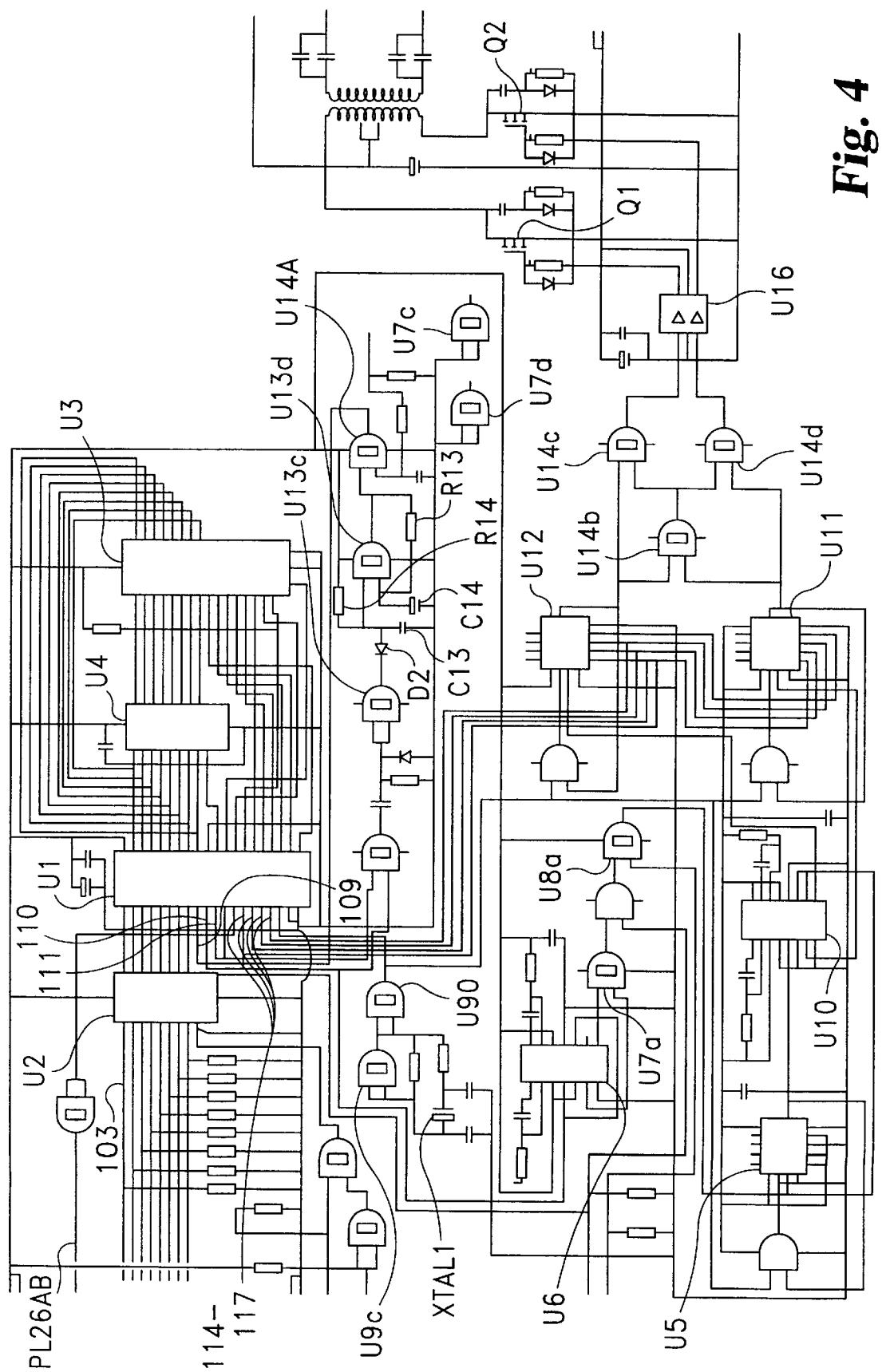
FIG. 4 illustrates an electrical circuit for the waveform generator of the invention in an illustrative form.

FIG. 4 illustrates in schematic form one embodiment of the electrical circuit of the waveform generator for the tool of the apparatus in an illustrative form only, but which is still part of the invention as claimed and wherein U1 is an 8031 Microcontroller that receives a code from the main control circuit as to which code is to be generated. The code is latched from the database by the local D type latch U2 when the select line 103 is taken high and the write line pulsed low by the main control board. The microcontroller programme is held in the EPROM U3 which is interfaced to U1 by the octal D-type latch U4. The clock signal for U1 is derived from an external clock circuit comprising XTAL1, U9C and U9D. This clock determines the fundamental frequency of the output waveform and is also connected to the counter circuits that generate the push pull drive pulses. The clock runs at 8.8 Mhz and results in a basic waveform frequency of 367 kHz.

The controller not only controls the output waveform but checks the integrity of the data bus lines. It does this by waiting for a specific byte to be received from the data bus. Once received the data test line on PL1/26AB is toggled to indicate to the main controller that it has been received. A succession of walking zero patterns are then sent by the main controller. As each pattern is received correctly PL26AB is toggled to indicate to the main controller to send the next byte. In this way all the eight data lines are checked to see that none are stuck high or low. Once the bus has been checked the main controller sends the pattern code. U1 then waits for the enable line to go high before generating an output on pin 110. Should valid data not be received as expected the whole bus test process is begun again before any output is generated on pin 110.

The output from pin 110 together with a 4-bit code on pins 114–117 contain the information necessary to create the push pull, pulse width controlled pair of signals necessary to drive the output power transistors. These push pull drive signals could not be generated directly from U1 because of the speed limitations of this particular microcontroller. Each rising or falling edge of the signal from pin 110 triggers a pair of push pull pulses generated by a logic controlled counter circuit. Pins 114–117 produce a 4-bit code that represents the pulse width of the push pull drive pulses. Counters U12 and U11 produce pulses whose width is set by the 4-bit data from pins 114–117 of U1.

Counter U5 sets the delay between a pulse from U12 beginning and a pulse from U11 beginning. U6 generates short pulses in response to the rising and falling edges on pin 110 necessary to load counters U12 and U5. U10 generates a short pulse after a delay generated by U5 necessary to load counter U11. U7a and U8a allow the enable and current limit signals to switch the pattern on and off by gating the load pulses to the counters. U7d together with U7c, U14b, U14c and U14d ensures that under no circumstances can simultaneous drive pulses be delivered to the power transistors which could result in their destruction. In any case simultaneous pulses from the counter circuits would indicate a circuit malfunction.

U16 is a MOSFET driver IC which produces the high current drive pulses for the output power transistors Q1 and Q2.

A watchdog circuit looks for activity on pins 110 and 111 of U1. Loss of activity on both of these lines would indicate a problem with the execution of the microcontroller programme.

Should activity cease (ie toggling of either pin), C13, which is normally kept discharged by U13c and D2 will charge up through R14 so allowing the simple oscillator formed by U13d, C14 and R13 to operate. The toggling of the output of U13d results in a toggling of the microcontroller reset line on pin 109 of U1 by U14a. This will cause a restart of the microcontroller programme. The microcontroller will be held in the reset state should the power good line go low which indicates a problem with the power supply line.

In order to allow the control means of the invention to be adaptive in terms of components which can be used as part of the control system and to allow different components from different manufacturers with different specifications to be incorporated without affecting the performance of the control means, a primary and secondary Fuzzy Logic Controller (FLC).

The primary FLC is largely devoted to creating and modifying the fuzzy control rules relating to the system performance, and the secondary, or adaptive FLC is provided to allow the primary fuzzy set, membership functions, and control rules; in general the control means, to be modified and adapted to meet the design requirements of the control means and to allow changes in components and/or systems used to be taken into account without affecting the performance of the apparatus for the user.

Thus the adaptive FLC is provided to provide any of, generate new fuzzy rules as required, modify existing fuzzy rules, modifying defined fuzzy data sets, adjusting the membership functions, adjusting the universe of discourse and adjusting the scaling factors or control resolutions. The adaptive FLC comprises of a performance measurement module at the top level, a supervising and tuning module at the top level and an FLC at the low level.

The kernel of the adaptive FLC is a supervising and tuning module which determines the required modifications or adjustments to the corresponding parameters, based on the system performance measures.

A number of performance measures have been used to determine the system performance, including the process error, the change error, the least square error [LSE], the least mean square error [LMSE], and the mean square error [MSE], etc. [The LSE, LMSE and MSE algorithms are inherently heavy computationally].

The adaptive FLC operates with universe of discourse tuning. This allows adaptive control of the control means output parameters by using the variable universe of discourse approach. In this approach, the universe of discourse is widened or narrowed according to the performance measure, e.g. the magnitude of error, while the fuzzy control rules, once established remain unchanged.

The concept of this approach is an extension of the windowing technique of refining the fuzzy control rules in a prescribed region [or window]. In the specified window, the fuzzy control rule base is designed so that it corresponds to the finer fuzzy sets in a local universe of discourse and is treated as a subcontrol rule base. The subcontrol rule base will not be activated until the system reaches a state of close by control. As described with reference to FIGS. 5 and 6.

A number of factors have been considered during the FLC design using the windowing technique, these are;

1. Scaling factors, for the input/output variables.
2. The fuzzy sets defined for the input/output variables in the specific window.
3. The universe of discourse for the input/output variables in the specific window.
4. The subcontrol rules in the specified window.
5. The switching points between the window and global control.

When the subcontrol rule base in the window is the same as the global control rule base, variable universe of discourse are in effect being used since the fuzzy sets in the window base are defined in a different universe of discourse. Thus a different group of scaling factors [control resolution] for input/output variables can be expected.

The fuzzy tool [DCU programming language and compiler] has been used to acquire the fuzzy KB and to generate the fuzzy reasoning module which is used during the real time control stage of the apparatus output parameters.

Furthermore, the control means includes a fuzzy logic processor (FLP) which operates in conjunction with the fuzzy logic controllers to provide the required operation of the system. The FLP is included using the PVCRI inference scheme for MAX-MIN fuzzy reasoning with inference control rules as follows;

IF X1 is A11 AND X2 is A21 THEN Y is B1
IF X1 is A12 AND X2 is A22 THEN Y is B2

The X1 and X2 are the fuzzified input signals and Y is the output signal, and Aij and Bj are defined in their respective universe of discourse according to fuzzy logic rules. Each set is an array indexed by crisp value for each respective set according to cover complete universe of discourse rules. Any measured inputs will return a non-zero membership for a number of fuzzy sets. The functional architecture of the fuzzy inference mechanism is based on the illustration below. The MIN-MAX approach adopted allows binary level OR and AND gates to be realised.

Preferably a NEUROLOGIX; NLX230; FUZZY LOGIC ENGINE is used to implement a fuzzy KB memory, a fuzzy Inference Unit and a Controller. The fuzzy KB memory stores the fuzzy membership function and fuzzy rules in both RAM and ROM. Read Only Memory [ROM] from the Default Clinical Database. Random Access Memory [RAM] from the FLE and Adaptive Output parameter Filters [AOF].

Two main factors represent the fuzzy logic KB memory. The first is the membership map MAPSIZE. The second, the number of different levels the membership function takes, Nmem. The membership function value zero is represented as O, and the membership function value of 1 is represented by (Nmem-1).

The fuzzy inference unit has been set-up to handle two operations—MIN for fuzzy intersection and MAX for fuzzy union as shown in FIG. 7.

The inference subsystem incorporates fuzzy reference rules and the interface for inputs from the Main controller board, V/I Sense board, Pattern Generator and Output boards of the apparatus. To maintain flexibility rule memory is stores in ROM and RAM. Which board accesses ROM or RAM is controlled by a latch which is written to by the 8031 Main control unit. Using the RAM provides maximum flexibility in developing the fuzzy rule base in real time. The FLE is provided with input values from the default and adaptive input buffers.

Effectively the FLE appears to the control means 32 input/output addresses. A jumper on the board allows 16-bit inputs and outputs to be selected, and this enabled for speed of processing. The addresses used are;

300H Address latch Written to by V/IB, MCB, W/OB
301H Data latch input/output
302H Control latch Written to by V/IB, MCB, W/OB Due to potential timing conflicts between the FLE, the KB memory, and the control means host system, and the need to allow both the FLE and the control means to act as bus masters on the KB memory bus, the interface contains a number of latches which are set up synchronously with respect to the FLE by the control means. The most important of these is the control latch, which can be used to halt the FLE and tri-state its output buffers on the KB memory. The control latch is also used to enable the other buffers which allow KB memory or the FLE interface bus to be connected to a satellite computer system via MODEM. The outputs of the control latch are used to provide overall control of the buffers and latches as follows;

In a normal operating mode the control means operates as follows wherein $C\_1=$) and $C\_2=1$. This enables the buffers, and also U118 and U117 to connect the latches to the control means system interface bus, while disabling U109, U110, U113, and U114 so that the latches are isolated from the KB RAM.

Control Functions Normal KB Read Write
Latch mode update
Output [FLE]

C_1 mode 0 1 X X
C_2 /Mode 1 0 X X
C_3 Direction X X 1 0
C_4 /Direction X X 0 1
C_5 E1 on FLE X 1 101* 1
C_6 E2 on FLE X 1 1 101*
C_7 /CE on FLE 0 1 X X
C_8 Data out X X 101* 0
latch
C_9 /OE KB RAM 0 X 1 1
C_10 /WE KB RAM 1 X 1 0
*=the signal changes in order to latch data
X=do not care While in this mode, the following Control_Latch values are unchanged:
C_1: =0, C_2: =1;Enable appropriate buffers
C_7: =0;/CE on so FLE System interface bus is working
C_9: =0, C_10: =1;O/E on and /WE off for KB RAM
 ;KB RAM is in'
The following Control_Latch values are set-up initially;
C_3: =1, C_4: =O;
C_5: =1, C_6: =1;E1 and E2 off
C_8: =0;Output latch not enabled
Data is written to shared RAM by the following;
Address_Latch: =desired address
Data_Latch=desired Data
C_3: =0, C_4: =1;Set buffer directions
C_6: =0;Toggle E2 to
C_6: =1;Latch the data into the FLE
Read operation from the shared RAM by the following;
Address_Latch: =desired address
C_3: =1, C_4: =0;Set buffer directions
C_5: =0;E1, to output data
C_8: =1;Toggle output latch to
C_8: =0;Latch data into output latch
C_5: =1;Switch off E1
Pcvar: =Data_Latch;PC reads from data latch In an update mode of operation to read or write KB RAM from the PC, the buffers connecting the PC to the KB RAM are enabled and those connecting the FLE to the KB RAM and to the interface bus are disabled, by setting $C\_1$: =1 and $C\_2$: =0.

While in the KB RAM access mode, the following Control_Latch values are unchanged;
C_1: =0, C_2: =1;Enable appropriate buffers
C_5: =1, C_6: =1,
C_7: =1;/CE, E1, E2 off so FLE interface bus is off
The following Control_Latch bus is set-up as:
C_9: =1, C_10: =1;O/E and /WE off on KB RAM
C_3: =1, C_4: =0;
C_8: =0;output latch not enabled
The KB RAM write operation to write data to KB RAM involves the following steps;
Address_Latch: =desired address
Data_Latch: =desired Data
C_3: =0, C_4: =1;Set buffer directions
C_10: =0;Toggle /WE to
C_10: =1;Latch the data into KB RAM
The read operation involves the following steps;
Address_Latch: =desired address
C_3: =1, C_4: =0;Set buffer directions
C_9: =0;/OE on, to output data
C_8: =1;Toggle output latch to
C_8: =0;Latch data into output latch
C_9: =1;Switch off/OE
Pcvar: =Data_Latch;PC reads from data latch This decouples the PC data bus timing from the FLE system. The latches on the bus are fast enough to deal with the fastest systems currently available. Data is latched from the PC bus using a strobe [/IOW v /ADDRESS_DECODE] and output onto the PC bus using a strobe [/IOR v /ADDRESS_DECODE] where ADDRESS_DECODE refers to the decoded address signal from U4.

No use is made of the /INT, /IDLE or /STAT outputs of the FLE. All data transfers to PC via Modem or direct take place when the FLE has halted following a completion of an inference cycle. As the /IDLE line is not used, whether the FLE is running or halted can only be determined by reading the Output Communication Register, which is at address 1 of shared RAM, and ensuring that at the end of inferencing, just before it hals, the FLE changes the contents of this address. By polling the OCR for this change, the PC can detect whether the FLE has halted.

The apparatus as herein described therefore represents a substantial step forward in the provision of electrosurgical apparatus and methods of monitoring the same. In a first aspect there is provided the apparatus, which can include the tool for cutting and coagulating having a power supply provided thereto and also acting to allow measurement of the phase angle and the modulus of the impedance of the body tissue by the control means thereby removing the patient from the electrical circuit and hence the discarding of the the plate used in monopolar techniques, allows the risk of burns to areas of the patient to be eliminated. At the same time the possibility of occurence of capacitive coupling and/or leakage of current and interference with ancillary equipment such as cameras and ECG monitors is reduced.

In a second aspect there is provided a monitoring and analysis control means whereby the conditions of the tissue in which the tool is operating can be monitored by measuring the phase angle and the modulus of the impedance of the body tissue via the feedback signal and, by the analysis methods described above, altering, if required, the power output sent to the tool which ensures that the optimum power is sent to the tool tip hence easing the job of the surgeon and at the same time minimising the damage to the tissue surrounding the area by ensuring that the power output is not excessive.

Further advantages which result from use of this apparatus in comparison with conventional techniques are that there is a minimised zone of thermal Necrosis and the depth of cutting and coagulations can be more accurately controlled irrespective of the electrode type, size and output power, due to the ability to monitor, compare measurements and adjust the power supply during the operation of the tool.

The system can be used with conductive fluids when operating in a fluid environment as the patient is removed from the electric circuit without risk to the patient thereby allowing less harmful fluids to be used and the running costs of the apparatus are substantially reduced over conventional apparatus and at substantially lower power than the monopolar systems while allowing the same operations to be performed thereby reducing the risk of burns to patients and, yet further, secondary muscle or nerve stimulation. Furthermore additional, expensive monitoring equipment is not required.

I claim:

1. A method for the control of the power supply to the cutting tip of electrosurgical apparatus characterized in that the method includes applying a tool (2) with cutting tip (4) in position relative to the body tissue to commence work, measuring the phase angle and the modulus of the impedance indicative of the body tissue in a control means (6) connected to said tool (2), assessing the measurement in the control means (6) in conjunction with preceding impedance measurements and, if required, altering the power supply to the tool tip (2), and repeating the process at stages during use of the apparatus to ensure that the optimum cutting power is supplied at each instant.

2. A method according to claim 1, characterised in that the feedback information received is allocated into a series of blocks, said blocks held in the memory of the control means and updated as further measurements are received.

3. A method according to claim 2 characterised in that each of the information blocks is representative of a time interval and a set number of blocks are analysed in combination at any one time.

4. A method according to claim 3 characterised in that new measurements are allocated to a new block and at the same time the oldest block of information is removed from the groups of the blocks of information to be assessed at that instant.

* * * * *